(12) United States Patent
Vidaurri et al.

(10) Patent No.: US 6,331,608 B1
(45) Date of Patent: Dec. 18, 2001

(54) PROCESS FOR PRODUCING POLY (ARYLENE SULFIDE)

(75) Inventors: Fernando C. Vidaurri; Jon F. Geibel; James W. Waterman; Jay M. Chaffin; Aubrey South, Jr., all of Bartlesville, OK (US); Jeffrey S. Fodor, Borger, TX (US); Glenn F. Kile, Bartlesville, OK (US)

(73) Assignee: Phillips Petroleum Company, Bartlesville, OK (US)

( * ) Notice: Subject to any disclaimer, the term of this patent is extended or adjusted under 35 U.S.C. 154(b) by 0 days.

(21) Appl. No.: 09/394,790

(22) Filed: Sep. 13, 1999

(51) Int. Cl.[7] ..................................................... C08G 75/14
(52) U.S. Cl. ......................... 528/388; 528/491; 528/495; 528/499; 528/502 R; 528/502 D; 528/503
(58) Field of Search ..................................... 528/388, 491, 528/495, 499, 502 R, 502 D, 503

(56) References Cited

U.S. PATENT DOCUMENTS

| | | | |
|---|---|---|---|
| 3,800,845 | 4/1974 | Scoggin | 159/47 |
| 4,415,729 | 11/1983 | Scoggins et al. | 528/388 |
| 4,500,702 | 2/1985 | Ostlinning et al. | 528/388 |
| 4,789,729 | 12/1988 | Nagira et al. | 528/496 |
| 5,071,949 | 12/1991 | Nakamura et al. | 528/388 |
| 5,128,445 | 7/1992 | Scoggins et al. | 528/492 |
| 5,200,499 | 4/1993 | Geibel et al. | 528/388 |
| 5,231,163 | 7/1993 | Kosaka et al. | 528/388 |
| 5,241,043 | 8/1993 | Senga | 528/388 |
| 5,278,283 | 1/1994 | Miyoshi et al. | 528/388 |

*Primary Examiner*—Duc Truong
(74) *Attorney, Agent, or Firm*—Polly C. Owen

(57) ABSTRACT

A process is provided to recover at least one modifier compound and at least one polar organic compound from a reaction mixture comprising high molecular weight Poly (arylene sulfide) product, low molecular weight P(AS), cyclic and linear P(AS) oligomers, at least one POC, at least one modifier, an alkali metal halide by-product, and water.

20 Claims, No Drawings

US 6,331,608 B1

PROCESS FOR PRODUCING POLY (ARYLENE SULFIDE)

FIELD OF INVENTION

This invention relates to the field of processes for producing poly(arylene sulfide), hereinafter referred to as P(AS).

BACKGROUND OF THE INVENTION

The production of P(AS) for a variety of industrial and commercial uses has been known for some time. P(AS) is moldable into various articles including, but not limited to, parts, films, and fibers by means of, for example, injection molding and extrusion molding techniques. These articles have utility in a variety of applications where heat and chemical resistance properties are desired. For example, P(AS) can be utilized as a material for preparing electrical and electronic parts and automotive parts.

Generally, P(AS) is prepared by contacting reactants comprising at least one halogenated aromatic compound, at least one polar organic compound, hereinafter referred to as POC, at least one sulfur source, and at least one base under polymerization reaction conditions. Molecular weight modifier compounds can be added to produce high molecular weight P(AS). The most preferred modifier compound is sodium acetate due to its availability and effectiveness.

There are several problems associated with the synthesis of high molecular weight P(AS) that can cause production expenses to be high. First, in a quench recovery P(AS) process, there is a 5% to 15% reduced feedstock conversion to P(AS) product due to the loss of low molecular weight P(AS) and cyclic and linear P(AS) oligomers in a waste stream called "slime". Typically, this waste stream often is disposed in landfills or other disposal facilities. Secondly, the modifier compound utilized to synthesize high molecular weight P(AS) often is used only once in a polymerization process and is not captured and recycled for subsequent use. This constitutes a great expense in P(AS) production due to higher feedstock and waste disposal costs. Thirdly, the POC utilized in the process can be recovered, but often at a high cost. For example, n-hexanol often is utilized to extract N-methyl-2-pyrrolidone, a common POC. Operating a hexanol extractor system can require handling as much as 30 to 40 pounds of n-hexanol per pound of P(AS) produced causing high equipment and operational costs.

This invention provides a P(AS) process which recovers low molecular weight P(AS) and cyclic and linear P(AS) oligomers for future use. In addition, this invention provides a method for recovering the modifier compound, which greatly reduces feedstock and disposal expenses compared to current P(AS) processes. This invention also provides a more efficient means to recover the POC utilized in the process. Finally, as a result of these improvements, the P(AS) produced by this invention has higher purity than that produced from current P(AS) processes.

SUMMARY OF THE INVENTION

It is an object of this invention to provide a process to produce P(AS).

It is another object of this invention to provide a process to recover at least one modifier compound and at least one POC.

It is yet another object of this invention to provide a process that efficiently separates high molecular weight P(AS) from low molecular weight P(AS) and cyclic and linear P(AS) oligomers.

It is still another object of this invention to provide a process that produces high purity, high molecular weight P(AS) product.

In accordance with a first embodiment of the present invention, a process is provided comprising (or optionally, "consisting essentially of" or "consisting of") the sequential steps of:

1) cooling said P(AS) reaction mixture comprising high molecular weight poly(arylene sulfide), low molecular weight poly(arylene sulfide), cyclic and linear poly (arylene sulfide) oligomers, at least one polar organic compound, at least one modifier compound, an alkali metal halide by-product, and water to a temperature sufficient to solidify said high molecular weight poly (arylene sulfide) to produce a cooled reaction mixture;
2) venting said cooled reaction mixture to remove a majority of the water from said cooled reaction mixture to produce a cooled, dehydrated reaction mixture.

In accordance with a second embodiment of this invention, a process is provided comprising (or optionally, "consisting essentially of" or "consisting of"):

1) contacting said cooled, dehydrated reaction mixture with methanol to produce a methanol-rich mixture;
2) separating said methanol-rich mixture to produce a high molecular weight poly(arylene sulfide) product, a recycle mixture, and optionally, a low molecular weight poly(arylene sulfide) stream;
   wherein said recycle mixture comprises methanol, said polar organic compound, and said modifier compound;
   wherein said low molecular weight poly(arylene sulfide) stream comprises low molecular weight poly (arylene sulfide) and cyclic and linear poly(arylene sulfide) oligomers.

In accordance with a third embodiment of this invention, a process is provided comprising (or optionally, "consisting essentially of" or "consisting of"):

1) contacting said cooled, dehydrated reaction mixture with said polar organic compound to produce a polar organic compound-rich mixture;
2) separating said polar organic compound-rich mixture to produce a solid stream and a liquid stream;
   wherein said solid stream is in a substantially solid form and comprises high molecular weight poly (arylene sulfide), said polar organic compound, said modifier compound, and said alkali metal halide by-product;
   wherein said liquid stream is in a substantially liquid form and comprises substantially all of said low molecular weight poly(arylene sulfide) and cyclic and linear poly(arylene sulfide) oligomers, said polar organic compound, and said modifier compound;
3) contacting said solid stream with methanol to produce a methanol-rich poly(arylene sulfide) product mixture; and
4) separating said methanol-rich poly(arylene sulfide) product mixture to produce a high molecular weight poly(arylene sulfide) product and a recycle mixture;
   wherein said recycle mixture comprises methanol, said polar organic compound, and said modifier compound. In accordance with a fourth embodiment of this invention, a process is provided comprising (or optionally, "consisting essentially of" or "consisting of"):

1) contacting said liquid stream with methanol to produce a methanol-rich low molecular weight poly(arylene sulfide) mixture;

2) separating said methanol-rich low molecular weight poly(arylene sulfide) mixture to produce a low molecular weight poly(arylene sulfide) product and a recycle stream;

wherein said recycle stream comprises methanol, polar organic compound, and said modifier compound; and wherein said low molecular weight poly(arylene sulfide) product comprises said low molecular weight poly(arylene sulfide) and cyclic and linear poly(arylene sulfide) oligomers;

These objects and other objects of this invention will become more apparent with reference to the following.

DETAILED DESCRIPTION OF THE INVENTION

Different embodiments of this invention provide processes for producing P(AS) and recovering at least one modifier and at least one POC. The first step of a first embodiment of this invention comprises cooling a P(AS) reaction mixture to a temperature sufficient to cause the high molecular weight P(AS) to solidify to produce a cooled reaction mixture.

At the termination of a P(AS) polymerization reaction, the P(AS) reaction mixture comprises high molecular weight P(AS), low molecular weight P(AS), cyclic and linear P(AS) oligomers, at least one POC, at least one modifier compound, an alkali metal by-product, and water. The P(AS) reaction mixture is in a substantially liquid form at reaction temperatures. Alkali metal halide by-product is present as a precipitate.

The P(AS) reaction mixture is cooled to a temperature sufficient to cause the high molecular weight P(AS) to solidify into granules. U.S. Pat. Nos. 4,414,729 and 5,128,445 describe this process, and both patents are herein incorporated by reference. Generally, the reaction mixture is cooled to below about 240° C. to solidify the high molecular weight P(AS) into granules. Preferably, said reaction mixture is cooled to a temperature in a range of about 100° C. to about 240° C. If the temperature is lowered below 100° C., the latent heat is reduced thereby preventing proper removal of water in a venting step described later in this disclosure. Temperatures above 240° C. can prevent separation of the high molecular weight P(AS) from the low molecular weight P(AS) and linear and cyclic P(AS) oligomers since the high molecular weight P(AS) is in solution. Most preferably, the P(AS) reaction mixture is cooled to a temperature in a range of 125° C. to 225° C. for efficient separation of the high molecular weight P(AS) from the low molecular weight P(AS) and linear and cyclic P(AS) oligomers.

P(AS) reaction mixtures useful in this invention can be produced by any method known in the art. Examples of the P(AS) reaction mixtures useful in this invention are those prepared according to U.S. Pat. Nos. 3,919,177; 4,038,261; 4,038,262; 4,116,947; 4,282,347 and 4,350,810; the entire disclosures of which are herein incorporated by reference.

Generally, P(AS) reaction mixtures useful in this invention are prepared by contacting a halogenated aromatic compound, at least one POC, at least one sulfur source, and at least one base under polymerization reaction conditions. To produce high molecular weight P(AS), a modifier compound can be used. The use of the modifier compound in the production of high molecular weight P(AS) is disclosed in U.S. Pat. Nos. 3,919,177 and 5,334,70, (which specifically disclosure polycphenylen sulfide) both herein incorporated by reference.

As used herein, the term "high molecular weight" or "high molecular weight P(AS)" means all P(AS) having molecular weights high enough to be commercially desirable and useable in an uncured state. Generally, the melt flow index of a high molecular weight P(AS) is less than about 3,000 g/10 minutes. As used herein, the term "low molecular weight" or "low molecular weight P(AS)" means all P(AS) having molecular weights low enough to be commercially undesirable and not useable in an uncured state. Generally, the melt flow index of a low molecular weight P(AS) is greater than about 3,000 g/10 minutes. Melt flow index is determined by the method of ASTM D 1238-86, Procedure B—Automatically Time Flow Rate Procedure, condition 316/5.0 modified to use a 5 minute preheat time, with values of flow rate expressed in units of grams per ten minutes (g/10 min).

Halogenated aromatic compounds suitable for producing reaction mixtures useful in this invention can be represented by the formula

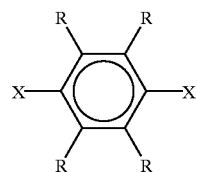

wherein X is a halogen, and R is selected from the group consisting of hydrogen, halogens, and alkyl, cycloalkyl, aryl, alkylaryl, and arylalkyl radicals having from about 6 to about 24 carbon atoms. Exemplary halogenated aromatic compounds include, but are not limited to, p-dichlorobenzene (DCB), p-dibromobenzene, p-diiodobenzene, 1-chloro-4-bromobenzene, 1-chloro-4-iodobenzene, 1-bromo-4-iodobenzene, 2,5-dichlorotoluene, 2,5-dichloro-p-xylene, 1-ethyl-4-isopropyl-2,5-dibromobenzene, 1,2,4,5-tetramethyl-3,6-dichlorobenzene, 1-butyl-4-cyclohexyl-2,5-dibromobenzene, 1-hexyl-3-dodecyl-2,5-dichlorobenzene, 1-octadecyl-2,4-diiodobenzene, 1-chloro-2-phenyl-4-bromobenzene, 1,4-diiodo-2-p-tolylbenzene, 1,4-dibromo-2-benzylbenzene, 1-octyl-4-(3-methylcyclopentyl)-2,5-dichlorobenzene, and mixtures thereof. The preferred halogenated aromatic compound is DCB, due to availability, ease of use, and high polymerization productivity. The preferred alkali metal bisulfide is sodium bisulfide (NaSH) due to availability and low cost.

Suitable bases to produce the P(AS) reaction mixture are alkali metal hydroxides selected from the group consisting of lithium hydroxide, sodium hydroxide, potassium hydroxide, rubidium hydroxide, cesium hydroxide, and mixtures thereof. If desired, the base can be produced in-situ by reaction of the corresponding oxide with water. The preferred base is sodium hydroxide (NaOH) due to availability and ease of use.

At least one modifier compound is utilized to produce the P(AS) reaction mixture. The modifier compound is selected from the group consisting of alkali metal carboxylates, alkali metal halides which are soluble in the POC, water, and mixtures thereof.

Alkali metal carboxylate modifier compounds can be represented by the formula $R^1$-COOM, where $R^1$ of the modifier compound is a hydrocarbyl radical having from 1 to about 20 carbon atoms and is selected from the group consisting of alkyl, cycloalkyl, and aryl and combinations thereof such as alkylaryl, alkylcycloalkyl, cycloalkylalkyl, arylalkyl, arylcycloalkyl, alkylarylalkyl and alkylcycloalkylalkyl, and M is an alkali metal selected from the group consisting of lithium, sodium, potassium, rubidium and cesium. Preferably, in order to have a more efficient polymerization reaction, $R^1$ is an alkyl radical having from 1 to about 6 carbon atoms or a phenyl radical, and M is lithium or sodium. If desired, the alkali metal carboxylate modifier compound can be employed as a hydrate or as a solution or dispersion in water. If desired, the alkali metal carboxylate modifier compound can be produced in-situ by a reaction of the corresponding carboxylic acid and an alkali metal hydroxide or carbonate.

Suitable alkali metal carboxylate modifier compounds which can be employed to produce the P(AS) reaction mixture are selected from the group consisting of lithium acetate, sodium acetate, potassium acetate, lithium propionate, sodium propionate, lithium 2-methylpropionate, rubidium butyrate, lithium valerate, sodium valerate, cesium hexanoate, lithium heptanoate, lithium 2-methyloctanoate, potassium dodecanoate, rubidium 4-ethyltetradecanoate, sodium octadecanoate, sodium heneicosanoate, lithium cyclohexanecarboxylate, cesium cyclododecanecarboxylate, sodium 3-methylcyclopentanecarboxylate, potassium cyclohexylacetate, potassium benzoate, lithium benzoate, sodium benzoate, potassium m-toluate, lithium phenylacetate, sodium 4-phenylcyclohexanecarboxylate, potassium p-tolylacetate, lithium 4-ethylcyclohexylacetate, and mixtures thereof. The preferred alkali metal carboxylate modifier compound for use in this invention is sodium acetate (NaOAc) due to availability, low cost, and effectiveness.

Alkali metal halide modifier compounds useful in this invention are those which are soluble in the POC or can be made soluble in a mixture of the POC and another modifier compound. For example, lithium chloride can be useful as a modifier compound, since it is soluble in certain POCs, such as, for example, NMP.

The second step in this first embodiment comprises venting the cooled reaction mixture to remove a majority of the water and a portion of the halogenated aromatic compound from the cooled reaction mixture to produce a cooled, dehydrated reaction mixture. The P(AS) reaction mixture must be cooled prior to venting since venting at polymerization temperatures can prevent the high molecular weight P(AS) from forming granules, which is key to the physical separation of the high molecular weight P(AS) from the low molecular weight P(AS) and cyclic and linear P(AS) oligomers. This venting takes advantage of the latent heat of the cooled reaction mixture to remove a majority of the water and a portion of the halogenated aromatic compound. By venting the water, less water needs to be handled during recovery of the POC and modifier compound, as discussed later in this disclosure. This is a significant improvement to current P(AS) processes since removing water in order to recover the POC and modifier compound in later process steps can be highly energy intensive, and therefore, can increase production costs of P(AS). The halogenated aromatic compound can be condensed and recovered for reuse.

In a second embodiment of this invention, a process is provided to produce a high molecular weight P(AS) product and to recover the modifier compound and the POC. The first step of the second embodiment comprises contacting the cooled, dehydrated reaction mixture with methanol to produce a methanol-rich mixture. The use of methanol provides a method to recover the modifier compound and the POC since the modifier compound and the POC typically are soluble in methanol. Generally, the cooled, dehydrated reaction mixture is contacted with methanol at a temperature sufficient to remove a majority of the modifier compound and POC. Preferably, said cooled, dehydrated reaction mixture is contacted with methanol at a temperature in a range of about 20° C. to about 50° C. In this temperature range, losses of methanol are minimized.

Generally, about 1.5 to about 15 pounds of methanol per pound of P(AS) is used to recover the modifier compound and the POC. Preferably, about 7 to about 11 pounds of methanol per pound of P(AS) is used, and most preferably, 8 to 10 pounds of methanol per pound of P(AS). The preferred ranges are established to adequately and economically remove the modifier compound and the POC from the cooled, dehydrated reaction mixture.

Generally, the cooled, dehydrated reaction mixture is contacted with methanol a sufficient number of times to adequately remove a majority of the modifier compound and the POC. Preferably, the cooled, dehydrated reaction mixture is contacted with methanol in at least three repetitions. The cooled, dehydrated reaction mixture can be contacted with methanol by any method known in the art. For example, counter-current washing techniques can be utilized. In counter-current washing, the cooled, dehydrated reaction mixture flows in one direction, and the methanol flows in the opposite direction.

The second step of this second embodiment comprises separating the methanol-rich mixture to produce a high molecular weight P(AS) product and a recycle mixture, and optionally, a low molecular weight P(AS) stream. The recycle mixture comprises methanol, POC, and modifier compound. The low molecular weight P(AS) stream comprises low molecular weight P(AS), and cyclic and linear P(AS) oligomers. Separation can be accomplished by any process known in the art. For example, such processes can include, but are not limited to, centrifugation, filtration, and screening. Typically if screening is used, the recycle mixture can contain low molecular weight P(AS) and cyclic and linear oligomers, alkali metal halide by-product, and possibly undissolved modifier compound.

The high molecular weight P(AS) product can be contacted with water to produce a water-washed high molecular weight P(AS) product and an alkali metal halide by-product stream. The alkali metal halide by-product stream comprises water, methanol, and alkali metal halide by-product. The water-washed high molecular weight P(AS) product and alkali metal halide by-product then are separated by any process known in the art. For example, such processes can include, but are not limited to, centrifugation and filtration.

Various additives can be mixed with the high molecular weight P(AS) product obtained in the present invention. Common additives include, but are not limited to, inorganic fillers (e.g., glass fiber, carbon fiber, titanium oxide, calcium carbonate, etc.) antioxidants, heat stabilizers, ultraviolet absorbents, coloring agents, and mixtures thereof.

If necessary, other polymers such as, for example, polyamides, polysulfones, polycarbonates, polyether sulfones, polyethylene terephthalates, polybutylene terephthalates, polyethylenes, polypropylenes, polytetrafluoroethylenes, polyether ester elastomers, and polyether amide elastomers also can be added.

If desired, the high molecular weight P(AS) product also can be cured by heating at temperatures up to about 480° C. to provide cured products having improved properties and high thermal stability and good chemical resistance.

The recycle mixture can be separated in a first separation zone, optionally, in the presence of water, to yield methanol and a recycle feedstock mixture. The recycle feedstock mixture comprises POC and modifier compound. The first separation zone can comprise any means known in the art to separate the recycle mixture. Preferably, a fractionation column is utilized at sufficient temperatures and pressures to allow methanol to be recovered in one stream and the recycle feedstock mixture to be recovered in a different stream. Both the methanol and recycle feedstock mixture can be reused.

Removal of substantially all of the methanol from the recycle mixture can cause the modifier compound to precipitate. For example, since sodium acetate is not appreciably soluble in NMP, sodium acetate can precipitate when the methanol is removed. Preferably, said separation is conducted in the presence of water in order for the modifier compound to form a solution with water and POC, so that the solution can be more easily handled. Sufficient water should be added to adequately form the solution. Generally, about 2 to about 10 moles of water per mole of modifier compound are added to adequately form the solution. Preferably, about 3 to about 8 moles of water per mole of modifier compound are added, and most preferably, 4 moles to 6 moles of water per.

The alkali metal halide by-product stream can be separated in a second separation zone to produce methanol and a brine stream, wherein said brine stream comprises water and the alkali metal halide by-product. The second separation zone can comprise any means known in the art to separate the alkali metal halide by-product stream. Preferably, a fractionation column is utilized at sufficient temperatures and pressures to allow methanol to be recovered in one stream and the brine to be recovered in a different stream. The methanol can be reused.

In a third embodiment of this invention, a process is provided to produce a high molecular weight P(AS) product and to recover the modifier compound and the POC. The first step of the third embodiment of this invention comprises contacting the cooled, dehydrated reaction mixture with POC to produce a POC-rich mixture. The POC can be any POC previously discussed in this disclosure, and preferably, is NMP due to its availability and ease of use. Generally, the POC is at a temperature in a range of about 100° C. to about 220° C. Preferably, the POC is at a temperature in a range of about 135° C. to about 200° C., and most preferably, 150° C. to 175° C. At temperatures below about 135° C., the solubility of low molecular weight P(AS) in the POC is significantly lower. At temperatures above 200° C., if NMP is used as the POC, the vapor pressure of NMP can require that the contacting be conducted in a pressure vessel. The higher the temperature of contacting the cooled, dehydrated reaction mixture with POC, the greater the amount of low molecular weight P(AS) and linear and cyclic oligomers that can be removed from the cooled, dehydrated reaction mixture.

Preferably, sufficient POC should be added to produce a POC-rich mixture that adequately dissolves the low molecular weight P(AS) and linear and cyclic oligomers. This allows removal of substantially all of the low molecular weight P(AS) and cyclic and linear oligomers, thus producing a higher purity high molecular weight P(AS) product. Preferably, about 2 to about 7 moles of POC per mole of P(AS) should be added for adequate removal. Most preferably, 3 to 6 moles of POC per mole of P(AS) is used.

Generally, the cooled, dehydrated reaction mixture is contacted with POC at a temperature sufficient to dissolve substantially all of the low molecular weight P(AS) and cyclic and linear oligomers. The reaction mixture can be contacted with the POC multiple times to further remove the low molecular weight P(AS) and linear and cyclic oligomers.

Contacting times between the cooled, dehydrated reaction mixture and the POC should be sufficient to dissolve substantially all of the low molecular weight P(AS) and cyclic and linear oligomers. Contact times as short as 1 minute can be adequate to remove low molecular weight P(AS) and cyclic and linear oligomers from the cooled, dehydrated reaction mixture.

The second step of the third embodiment of this invention comprises separating the POC-rich mixture to produce a solid stream and a liquid stream. The solid stream is in a substantially solid form and comprises high molecular weight P(AS), POC, modifier compound, and alkali metal halide by-product. The high molecular weight P(AS) is in a substantially granular form. The liquid stream is in a substantially liquid form and comprises POC, modifier compound, and substantially all of the low molecular weight P(AS) and cyclic and linear P(AS) oligomers. The low molecular weight P(AS) is in the form of fine solids.

The separation should be completed at a temperature similar to the temperature at which the POC was contacted with the cooled, dehydrated reaction mixture. If the POC-rich mixture is cooled, the low molecular weight P(AS) and cyclic and linear oligomers can precipitate on the high molecular weight P(AS), thereby decreasing the efficiency of removal. The separation can be accomplished by any process known in the art. For example, screening can be used.

The third step of the third embodiment of this invention comprises contacting the solid stream with methanol to produce a methanol-rich P(AS) product mixture. The methanol is utilized to remove the POC and modifier compound from the high molecular weight P(AS). The same conditions as used in contacting the cooled, dehydrated reaction mixture with methanol can be used.

The fourth step of the third embodiment comprises separating the methanol-rich P(AS) product mixture to produce a high molecular weight P(AS) product and a recycle mixture. The recycle mixture comprises methanol, POC, and modifier compound. The separation can be accomplished by any process known by those of ordinary skill in the art. For example, such processes can include, but are not limited to, centrifugation, filtration, and screening systems.

The recycle mixture can be separated in the first separation zone to yield methanol and the recycle feedstock mixture. The first separation zone has been previously discussed in this disclosure.

Said high molecular weight P(AS) product can be handled as previously discussed in this disclosure.

In yet a fourth embodiment of this invention, a process is provided to recover methanol, sodium acetate, and POC from the liquid stream. The first step in the fourth embodiment comprises contacting the liquid stream with methanol to produce a methanol-rich low molecular weight poly (arylene sulfide) mixture. The same conditions as used in contacting the solid stream with methanol can be used.

The second step in fourth embodiment comprises separating said quench process methanol-rich low molecular weight poly(arylene sulfide) mixture to produce a low molecular weight poly(arylene sulfide) product and a recycle stream. The recycle stream comprises methanol, polar organic compound, and modifier compound. The low molecular weight poly(arylene sulfide) product comprises low molecular weight poly(arylene sulfide) and cyclic and linear poly(arylene sulfide) oligomers. The separation can be accomplished by any process known in the art. For example, such processes can include, but are not limited to centrifugation and filtration.

The recycle mixture can be separated in the first separation zone as discussed previously in this disclosure.

The low molecular weight poly(arylene sulfide) product can be contacted with water to produce a water-washed low molecular weight poly(arylene sulfide) product and an alkali metal halide by-product stream. The alkali metal halide by-product stream can be treated in the second separation zone as discussed previously in this disclosure.

EXAMPLES

Example 1

The following example shows that methanol can be separated from NMP by fractionation.

75 grams of methanol and 75 grams of NMP (Fisher Purified Grade) were added to a 250 milliliter round bottom flask containing boiling chips. The flask was attached to a vacuum jacketed fractionating column. Heat was applied to the round bottom flask using a heating mantle. The vacuum jacketed fractionating column heated slowly due to internal reflux. A vapor started to flow through a condenser and into a receiver to produce an overhead liquid stream. The flow of vapor slowed until the temperature of the fractionating column increased with further heating of the round bottom flask. Upon reaching the boiling point of NMP, the flow of the overhead liquid stream resumed. Then, the vacuum jacketed fractionating column was cooled to room temperature. Heating of the round bottom flash was then terminated.

Fractions of the overhead liquid stream were collected in small vials. These fractions and a sample of liquid remaining in the round bottom flask were analyzed using gas chromatography. Analyses of the fractions indicated that 99.547% by weight of the overhead liquid stream collected was methanol and 0.453% by weight was NMP. Analysis of the sample of the liquid in the round bottom flask was found to be 100% NMP.

Thus, methanol can be removed efficiently from NMP.

Example 2

This example shows separation of a recycle mixture to produce methanol and a recycle feedstock mixture.

A recycle mixture containing 78.03 wt. % NMP, 15.90 wt. % methanol, and 6.07 wt. % sodium acetate was fed to a laboratory continuous distillation kettle at a continuous rate of 504.20 cm$^3$/hr. A small quantity of NMP was initially added to the kettle. The kettle was heated until the recycle mixture reached reflux at which point the kettle temperature was approximately 210° C., and the temperature throughout the column was about 66–208° C. A methanol stream was recovered through an overhead splitter and routed to an overhead condenser, and then to an overhead receiver. The overhead splitter was set to collect for 0.2 minutes and to discharge to the overhead receiver for 5 seconds. The recycle feedstock mixture was pumped from the kettle at a rate of 87.40 cm$^3$/hr. After approximately one hour, samples were collected of the methanol stream and the recycle feedstock mixture in the bottom of the kettle.

The recycle feedstock mixture and methanol stream were analyzed by gas chromatography. The recycle feedstock mixture contained 99.50 wt. % NMP, 0.29 wt. % methanol, and 0.21 wt. % of other compounds. The methanol stream contained 99.73 wt % methanol, 0.08 wt. % NMP, and 0.19 wt. % other compounds.

During the experiment, it was noted by visual inspection that the sodium acetate accumulated in the bottom of the distillation kettle and column.

This example teaches that methanol can be removed efficiently from sodium acetate and NMP.

Example 3

This example demonstrates that water can be added to a recycle mixture to help prevent the accumulation of sodium acetate in the bottom of the distillation kettle.

The same procedures as disclosed in Example 2 were utilized except the recycle mixture contained 14.60 wt. % methanol, 72.00 wt. % NMP, 4.60 wt.% sodium acetate, and 8.8 wt. % water. The kettle temperature was approximately 190–198° C., and the temperature throughout the column was approximately 68–102° C. The overhead splitter was set to collect for 0.3 minutes and to discharge to the overhead receiver for 5 seconds Samples of the methanol stream and the recycled feedstock stream were collected after 8.66 hours of distillation and analyzed by gas chromatography. The recycle feedstock mixture contained 97.53 wt. % NMP, 0.00 wt. % methanol, 1.63 wt. % water, and 0.16 wt. % of other compounds. The methanol stream contained 97.36 wt % methanol, 0.03 wt. % NMP, 2.60 wt. % water, and 0.02 wt. % other compounds. Negligible precipitation of sodium acetate was observed in the bottom of the distillation kettle. Ion chromatograph was used to determine the amount of sodium acetate in the recycle feedstock mixture. 0.69 % by weight sodium acetate was found.

This experiment illustrates that the addition of water to the recycle mixture substantially prevents the accumulation of sodium acetate in the bottom of the distillation kettle. An exact mass balance was not achieved in this experiment for the sodium acetate since the distillation was not continued for a long enough duration.

While this invention has been described in detail for the purpose of illustration, it is not intended to be limited thereby but is intended to cover all changes and modifications within the spirit and scope thereof.

That which is claimed is:

1. A process to recover at least one polar organic compound and at least one modifier compound from a P(AS) reaction mixture, said process comprising the sequential steps of:
   1) cooling said P(AS) reaction mixture comprising high molecular weight poly(arylene sulfide), low molecular weight poly(arylene sulfide), cyclic and linear poly(arylene sulfide) oligomers, at least one polar organic compound, at least one modifier compound, an alkali metal halide by-product, and water to a temperature sufficient to solidify said high molecular weight poly(arylene sulfide) to produce a cooled reaction mixture;
   2) venting said cooled reaction mixture to remove a majority of the water from said cooled reaction mixture to produce a cooled, dehydrated reaction mixture.

2. A process according to claim 1 further comprising:
   1) contacting said cooled, dehydrated reaction mixture with methanol to produce a methanol-rich mixture;
   2) separating said methanol-rich mixture to produce a high molecular weight poly(arylene sulfide) product, a recycle mixture, and optionally, a low molecular weight poly(arylene sulfide) stream;
      wherein said recycle mixture comprises methanol, said polar organic compound, and said modifier compound;
      wherein said low molecular weight poly(arylene sulfide) stream comprises low molecular poly (arylene sulfide) and cyclic and linear poly(arylene sulfide) oligomers.

3. A process according to claim 2 further comprising separating said recycle mixture in a first separation zone, optionally, in the presence of water, to yield methanol and a recycle feedstock mixture;

wherein said recycle feedstock mixture comprises said polar organic compound and said modifier compound.

4. A process according to claim 3 further comprising contacting the high molecular weight poly(arylene-sulfide) product with water to produce a water-washed high molecular weight poly(arylene sulfide) product and an alkali metal halide by-product stream;

wherein said alkali metal halide by-product stream comprises water, methanol, and said alkali metal halide by-product.

5. A process according to claim 4 further comprising separating said alkali metal halide by-product stream in a second separation zone to produce methanol and a brine stream, wherein said brine stream comprises water and said alkali metal halide by-product.

6. A process according to claim 1 further comprising:
1) contacting said cooled, dehydrated reaction mixture with additional polar organic compound to produce a polar organic compound-rich mixture;
2) separating said polar organic compound-rich mixture to produce a solid stream and a liquid stream;
wherein said solid stream is in a substantially solid form and comprises high molecular weight poly(arylene sulfide), said polar organic compound, said modifier compound, and said alkali metal halide by-product;
wherein said liquid stream is in a substantially liquid form and comprises substantially all of said low molecular weight poly(arylene sulfide) and cyclic and linear poly(arylene sulfide) oligomers, said polar organic compound, and said modifier compound;
3) contacting said solid stream with methanol to produce a methanol-rich poly(arylene sulfide) product mixture; and
4) separating said methanol-rich poly(arylene sulfide) product mixture to produce a high molecular weight poly(arylene sulfide) product and a recycle mixture;
wherein said recycle mixture comprises methanol, said polar organic compound, and said modifier compound.

7. A process according to claim 6 further comprising separating said recycle mixture in a first separation zone, optionally, in the presence of water, to yield methanol and a recycle feedstock mixture;

wherein said recycle feedstock mixture comprises said polar organic compound and said modifier compound.

8. A process according to claim 7 further comprising contacting the high molecular weight poly(arylene sulfide) product with water to produce a water-washed high molecular weight poly(arylene sulfide) product and an alkali metal halide by-product stream;

wherein said alkali metal halide by-product stream comprises water, methanol, and said alkali metal halide by-product.

9. A process according to claim 8 further comprising separating said alkali metal halide by-product stream in a second separation zone to produce methanol and a brine stream;

wherein said brine stream comprises water and the alkali metal halide by-product.

10. A process according to claim 6 further comprising:
1) contacting said liquid stream with methanol to produce a methanol-rich low molecular weight poly(arylene sulfide) mixture
2) separating said methanol-rich low molecular weight poly(arylene sulfide) mixture to produce a low molecular weight poly(arylene sulfide) product and a recycle stream;
wherein said recycle stream comprises methanol, polar organic compound, and said modifier compound; and
wherein said low molecular weight poly(arylene sulfide) product comprises said low molecular weight poly(arylene sulfide) and cyclic and linear poly(arylene sulfide) oligomers.

11. A process according to claim 10 further comprising separating said recycle mixture in a first separation zone, optionally, in the presence of water, to yield methanol and a recycle feedstock mixture;

wherein said recycle feedstock mixture comprises said polar organic compound and said modifier compound.

12. A process according to claim 11 further comprising contacting said low molecular weight poly(arylene sulfide) product with water to produce a water-washed low molecular weight poly(arylene sulfide) product and an alkali metal halide by-product stream;

wherein said alkali metal halide by-product stream comprises water, methanol, and said alkali metal halide by-product.

13. A process according to claim 12 further comprising separating said alkali metal halide by-product stream in a second separation zone to produce methanol and a brine stream;

wherein said brine stream comprises water and alkali metal halide by-product.

14. A process according to claim 9 further comprising:
contacting said liquid stream with methanol to produce a methanol-rich low molecular weight poly(arylene sulfide) mixture;
separating said methanol-rich low molecular weight poly(arylene sulfide) mixture into a low molecular weight poly(arylene sulfide) product stream and a recycle stream comprising methanol, polar organic compound and modifier;
combining said recycle stream with said recycle mixture for separation in said first separation zone; and
recovering said low molecular weight poly(arylene sulfide) as a product of the process.

15. A process according to claim 1 wherein said reaction mixture is cooled to a temperature within the range of 100 C. to 240 C. prior to said venting.

16. A process according to claim 1 wherein said reaction mixture is cooled to a temperature within the range of 125 C. to 225 C. prior to said venting.

17. A process according to claim 1 wherein said poly(arylene sulfide) is poly(phenylene sulfide), said polar organic compound is NMP and said modifier compound is sodium acetate.

18. A process according to claim 6 wherein said reaction mixture is cooled to a temperature within the range of 125 C. to 225 C. prior to said venting.

19. A process according to claim 6 wherein said additional polar organic compound is at a temperature within the range of 100 C. to 240 C. at the time of said contacting.

20. A process to recover NMP and sodium acetate from a poly(phenylene sulfide) reaction mixture, said process comprising the sequential steps of:

1) cooling said poly(phenylene sulfide) reaction mixture comprising high molecular weight poly(phenylene sulfide), low molecular weight poly(phenylene sulfide), cyclic and linear poly(phenylene sulfide) oligomers, NMP, sodium acetate, sodium chloride by-product, and water to a temperature within the range of 125 C. to 225 C. so as to solidify said high molecular weight poly (phenylene sulfide) and thus produce a cooled reaction mixture;

2) thereafter venting said cooled reaction mixture to remove a majority of said water from said cooled reaction mixture to produce a cooled, dehydrated reaction mixture;

said process further comprising:

3) contacting said cooled, dehydrated reaction mixture with additional NMP which additional NMP is at a temperature within the range of 125 C. to 225 C. to produce an NMP-rich mixture;

4) separating said NMP-rich mixture to produce a solid component and a liquid stream;

wherein said solid component comprises high molecular weight poly(phenylene sulfide), NMP, sodium acetate, and sodium chloride by-product; wherein said liquid stream is in a substantially liquid form and comprises substantially all of said low molecular weight poly (phenylene sulfide) and cyclic and linear poly (phenylene sulfide) oligomers, NMP, sodium acetate and sodium chloride by-product;

5) contacting said solid component with methanol to produce a methanol-rich poly(phenylene sulfide) product mixture;

6) separating said methanol-rich poly(phenylene sulfide) product mixture to produce a high molecular weight poly(phenylene sulfide) product stream and a recycle feedstock mixture stream;

wherein said recycle feedstock mixture stream comprises methanol, NMP, and sodium acetate;

7) passing said recycle feedstock mixture stream to a first separation zone for separation into a methyl alcohol stream and a stream comprising NMP and sodium acetate, and recovering said NMP and sodium acetate as products of the process;

8) contacting said high molecular weight poly(phenylene sulfide) product stream with water to produce a water-washed high molecular weight poly(phenylene sulfide) product stream and a sodium chloride by-product stream, wherein said sodium chloride by-product stream comprises water, methanol, and sodium chloride;

9) contacting said liquid stream of step 4 with methanol to produce a methanol-rich low molecular weight poly (phenylene sulfide) mixture;

10) separating said methanol-rich low molecular weight poly(phenylene sulfide) mixture to produce a low molecular weight poly(phenylene sulfide) product stream and a recycle stream;

wherein said recycle stream comprises methanol NMP, and sodium acetate; and wherein said low molecular weight poly(arylene sulfide) product comprises said low molecular weight poly (phenylene sulfide) and cyclic and linear poly (phenylene sulfide) oligomers;

11) separating said sodium chloride by-product stream of step 8 in a second separation zone to produce methanol stream and a brine stream; wherein said brine stream comprises water and sodium chloride by-product;

12) combining said recycle stream of step 10 with said recycle feedstock mixture stream of step 6; and 13) contacting said low molecular weight poly(arylene sulfide) product stream of step 10 with water to produce a water-washed low molecular weight poly(arylene sulfide) product stream and a sodium chloride by-product stream;

wherein said sodium chloride by-product stream comprises water, methanol, and said sodium chloride by-product and wherein said sodium chloride by-product stream is combined with said sodium chloride by-product stream of step 8.

* * * * *